United States Patent
Shin et al.

(10) Patent No.: US 8,473,025 B2
(45) Date of Patent: Jun. 25, 2013

(54) ELECTRODE FOR LIVING BODY AND DEVICE FOR DETECTING LIVING SIGNAL

(75) Inventors: Kun Soo Shin, Seongnam-si (KR); Jin Sang Hwang, Suwon-si (KR); Jong Pal Kim, Seoul (KR); Hyung Sok Yeo, Yongin-si (KR); Sang Ryong Kim, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 13/473,258

(22) Filed: May 16, 2012

(65) Prior Publication Data

US 2012/0226128 A1  Sep. 6, 2012

Related U.S. Application Data

(62) Division of application No. 12/588,694, filed on Oct. 23, 2009, now Pat. No. 8,214,009, which is a division of application No. 11/487,316, filed on Jul. 17, 2006, now Pat. No. 7,668,580.

(30) Foreign Application Priority Data

Oct. 20, 2005 (KR) ........................ 10-2005-0099018
May 8, 2006 (KR) ........................ 10-2006-0041143

(51) Int. Cl.
*A61B 5/04* (2006.01)
(52) U.S. Cl.
USPC ............ 600/391; 600/392; 600/393; 600/394
(58) Field of Classification Search
USPC ................................. 600/391–394
See application file for complete search history.

(56) References Cited

U.S. PATENT DOCUMENTS

| | | | |
|---|---|---|---|
| 4,239,046 A | 12/1980 | Ong | |
| 4,274,420 A | 6/1981 | Hymes | |
| 4,398,545 A | 8/1983 | Wilson | |
| 4,576,170 A | 3/1986 | Bradley et al. | |

(Continued)

FOREIGN PATENT DOCUMENTS

| | | |
|---|---|---|
| EP | 0276661 | 1/1988 |
| JP | 63-114605 | 7/1988 |

(Continued)

OTHER PUBLICATIONS

Office Action mailed Jun. 12, 2008 in U.S. Patent No. 7,668,580.

(Continued)

*Primary Examiner* — Lee S Cohen
(74) *Attorney, Agent, or Firm* — Staas & Halsey LLP

(57) ABSTRACT

A biosignal measurement device includes an electrode and a signal processing member. The electrode includes an insulation sheet having a hole, a device contact portion provided on the top surface of the insulation sheet and a body contact portion provided on the bottom surface of the insulation sheet, the device contact portion and the body contact portion electrically connected to each other via the hole. The signal processing member includes an externally exposed terminal to make surface contact with the device contact portion, an analog signal processing unit, an A/D signal converter and a digital signal processing unit. Also, the device contact portion and the body contact portion are formed of a material which is both conductive and adhesive. Accordingly, the signal processing member may be directly attached. Noise may be reduced. Also, a biosignal may be accurately measured.

12 Claims, 12 Drawing Sheets

U.S. PATENT DOCUMENTS

| | | | |
|---|---|---|---|
| 4,643,193 | A | 2/1987 | DeMarzo |
| 4,865,039 | A | 9/1989 | Dunseath |
| 4,915,656 | A | 4/1990 | Alferness |
| 4,953,552 | A * | 9/1990 | DeMarzo .................... 600/391 |
| 5,085,217 | A | 2/1992 | Shimzu |
| 5,850,920 | A | 12/1998 | Gilman et al. |
| 5,891,028 | A | 4/1999 | Lundbäck |
| 6,148,233 | A | 11/2000 | Owen et al. |
| 6,415,170 | B1 | 7/2002 | Loutis et al. |
| 6,643,541 | B2 | 11/2003 | Mok et al. |
| 7,215,989 | B1 | 5/2007 | Burks |
| 7,373,196 | B2 | 5/2008 | Ryu et al. |
| 7,668,580 | B2 | 2/2010 | Shin et al. |

FOREIGN PATENT DOCUMENTS

| | | |
|---|---|---|
| JP | 02-79905 | 3/1990 |
| JP | 02-82310 | 6/1990 |
| JP | 04-067841 | 3/1992 |
| JP | 08-322812 | 12/1996 |
| JP | 09-253219 | 9/1997 |
| JP | 2002-233585 | 8/2002 |
| KR | 10-2005-0054773 | 6/2005 |
| KR | 10-2005-0121472 | 12/2005 |
| WO | 03/070097 | 8/2003 |

OTHER PUBLICATIONS

Office Action mailed Dec. 1, 2008 in U.S. Patent No. 7,668,580.

Office Action mailed Mar. 23, 2009 in U.S. Patent No. 7,668,580.

Advisory Action mailed May 14, 2009 in U.S. Patent No. 7,668,580.

Office Action mailed Jul. 23, 2009 in U.S. Patent No. 7,668,580.

Notice of Allowance mailed Nov. 6, 2009 in U.S. Patent No. 7,668,580.

Korean Office Action, mailed Apr. 26, 2007, in corresponding Korean Application No. 10-2005-0099018.

European Office Action in European Application EP 06 07 6565 (Search Completed Dec. 19, 2006).

Restriction Requirement mailed Sep. 20, 2010 in U.S. Appl. No. 12/588,694.

Office Action mailed Dec. 27, 2010 in U.S. Appl. No. 12/588,694.

Office Action mailed Dec. 27, 2011 in U.S. Appl. No. 12/588,694.

Notice of Allowance mailed Mar. 5, 2012 in U.S. Appl. No. 12/588,694.

U.S. Appl. No. 12/588,694, filed Oct. 23, 2009, Shin et al., Samsung Electronics Co., Ltd.

* cited by examiner

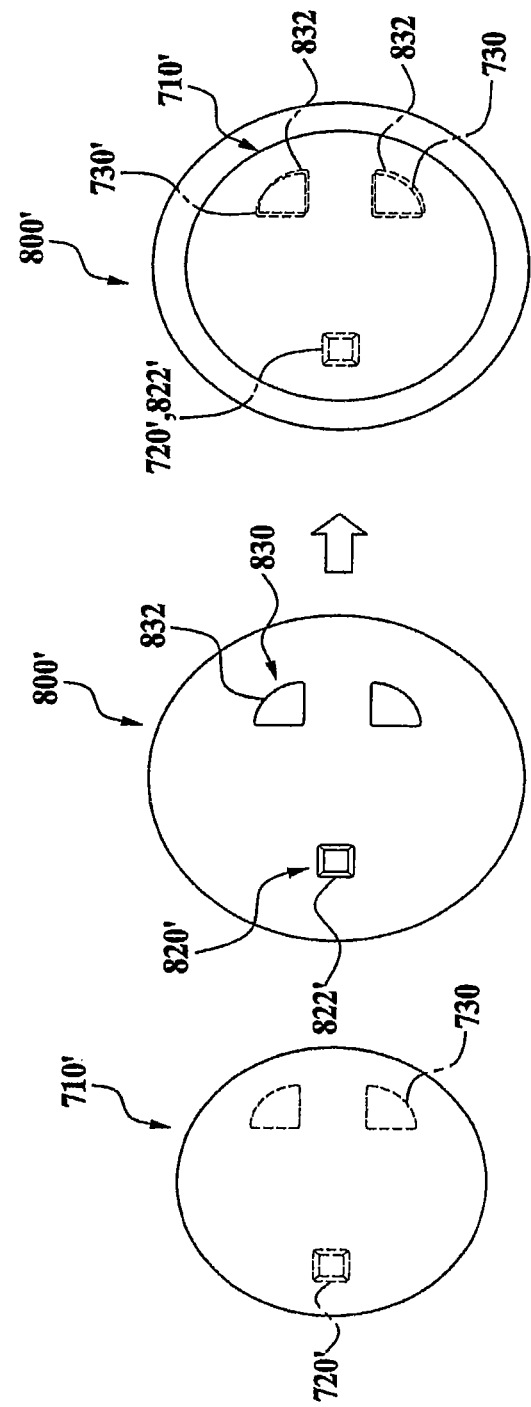

ELECTRODE FOR LIVING BODY AND DEVICE FOR DETECTING LIVING SIGNAL

CROSS-REFERENCE TO RELATED APPLICATIONS

This application is a divisional of prior application Ser. No. 12/588,694 filed on Oct. 23, 2009 in the U.S. Patent and Trademark Office (now U.S. Pat. No. 8,214,009, issued on Jul. 3, 2012), which is a divisional of prior application Ser. No. 11/487,316 filed on Jul. 17, 2006 in the U.S. Patent and Trademark Office (now U.S. Pat. No. 7,668,580, issued on Feb. 23, 2010), the disclosures of which are incorporated herein by reference. This application claims the priority benefit of prior application Ser. No. 12/588,694 and prior application Ser. No. 11/487,316. This application claims the priority benefit of Korean Patent Application No. 10-2005-0099018, filed Oct. 20, 2005 and Korean Patent Application No. 10-2006-0041143, filed May 8, 2006, in the Korean Intellectual Property Office, the disclosures of which are incorporated herein by reference.

BACKGROUND OF THE INVENTION

1. Field of the Invention

The present invention relates to an electrode for a living body, and more particularly, to an electrode which can transmit an electrical signal from a living body by using a simple electrode structure, and a biosignal measurement device using the electrode.

2. Description of Related Art

A living body is a kind of conductor and minute currents may occur in the living body. Accordingly, internal properties of the living body may be measured by sensing the minute currents from the living body and detecting a change of the minute currents with respect to an external stimulus. Generally, an electrocardiogram (ECG), an electromyogram (EMG), an electroencephalogram (EEG), a galvanic skin response (GSR), an eye electrooculogram (EOG), body temperature, pulse, blood pressure, body motion, etc. may be measured by using the above described principle. An electrode for a living body is used for sensing a change of a biosignal.

FIG. 1 is a perspective view illustrating a conventional electrode and biosignal measurement device, and FIG. 2 is a cross-sectional view illustrating an attachment state of the electrode of FIG. 1.

Referring to FIGS. 1 and 2, a conventional electrode 10 includes an adhesive sheet 20 and a metal electrode 30. The adhesive sheet 20 has insulating properties and is in the form of a round shape. The metal electrode 30 makes direct contact with a living body. Also, the metal electrode 30 is formed of a conductive material. The metal electrode 30 includes a contact portion 32 widely provided on the bottom surface of the adhesive sheet 20 and a protrusion 34 formed on the center of the contact portion 32. The protrusion 34 may be exposed to the outside of the adhesive sheet 20 via a hole. An adhesive material is formed on the bottom of the adhesive sheet 20. Accordingly, the electrode 10 may be closely attached onto the skin of a body.

A biosignal measurement device 1 includes a main controller 40, the electrode 10 and a cable 50. A socket 52 is provided at the end of the cable 52. A groove is formed in the socket 52 to be engaged with the protrusion 34. Accordingly, the socket 52 and the metal electrode 30 may be electrically connected to each other. The cable 50 may be connected to the electrode 10 via the socket 52. Also, the cable 50 may be connected to the main controller 40 via a plug provided opposite to the socket 52. When the electrode 10 is attached onto a living body, the main controller 40 may measure a biosignal. Also, the main controller 40 may measure an ECG, an EMG, an EEG, a GSR, an EOG, body temperature, etc. from the received biosignal.

Generally, the metal electrode 30 is directly exposed on the bottom of the electrode 10. While the adhesive sheet 20 is provided, a contact between the skin and the metal electrode 30 may not be stably maintained. Accordingly, a gel-typed electrolyte is spread over the skin. By using the gel-typed electrolyte as a medium, a relatively stabilized connection state may be maintained between the skin and the metal electrode 30.

However, although the gel-typed electrolyte is used, the connection using the conventional electrode may be easily affected by some factors that may interfere with a stable connection. As an example, while a biosignal is being transmitted from the skin through a process of skin-gel-metal electrode 30-socket 52-main controller 40, the biosignal may be weakened or noise may be introduced. Also, the metal electrode 30 and the socket 52 make point contact in the protrusion 34. Accordingly, an electrical connection state is very unstable. This can prevent an accurate measurement.

An electrode in the conventional art is made to be expendable and generally disposable, so a user uses a new electrode every time. Since frequent attachments and detachments between the socket and the electrode occur, unstable contact may often occur.

Also, a structure using the protrusion 34 and the socket 52 may be referred to as a snap connecting structure. The snap connecting structure is disadvantageous to miniaturize a biosignal measurement device. This is because the protrusion 34 is formed on the metal electrode 30 and thus, the electrode 10 may not be flattened. Also, since the socket 52 for electric connection occupies a considerable area for installation, the protrusions 34 of the electrode 30 should be separated at the minimal interval needed for installation of the socket 52, such that the electrode 30 may not be reduced.

Also, when integrating a plurality of electrodes onto a single body, a plurality of corresponding protrusions or snaps is required. Accordingly, the electrode or the device may not be easily miniaturized.

Also, when providing a plurality of snaps on a single body, an interval between each snap needs to be identical to an interval between sockets to be properly connected with the snaps. When the interval between the snaps is smaller than the interval between the sockets, the sockets may not be installed on an electrode. Also, when the interval between the snaps is larger than the interval between the terminals, connecting the sockets and snaps may cause the electrode to become deformed.

Accordingly, an electrode in a simple structure ensuring a stable connection, and that can also be easily miniaturized, is required.

BRIEF SUMMARY

An aspect of the present invention provides an electrode and a biosignal measurement device which can stably maintain the connection between the electrode and a cable.

An aspect of the present invention also provides an electrode and a biosignal measurement device having a simple structure which can transmit a minute current and prevent noise.

An aspect of the present invention also provides an electrode and a biosignal measurement device which can simultaneously provide a plurality of electrodes on one pad and also can be miniaturized and slimmed down.

An aspect of the present invention also provides an electrode and a biosignal measurement device in which the electrode can be easily installed on the device and replaced even when providing a plurality of terminals on a single electrode.

An aspect of the present invention also provides an electrode and a biosignal measurement device which can be functionally advantageous even when applied to a miniaturized device or a wearable device for measuring a biosignal.

According to an aspect of the present invention, there is provided an electrode for living body, including a sheet member formed of an insulating material and having a hole and an electrode member provided on the top and bottom surface of the sheet member via a hole. The electrode member includes a device contact portion making surface contact with a terminal of a biosignal measurement device on the top surface of the sheet member and a body contact portion making contact with the skin on the bottom surface of the sheet member. The device contact portion and the body contact portion are connected to each other via the hole. Also, since the device contact portion is formed of a conductive material, the device contact portion may be electrically connected to the terminal of the biosignal measurement device. Minute current transmitted from the skin is transferred via a simple path consisting of the electrode member and the terminal. In this case, the electrode member and the terminal are connected to each other by not point contact but surface contact. Accordingly, a signal-to-noise (S/N) ratio may be improved.

The device contact portion and the body contact portion may be formed of a material which is both conductive and adhesive. Also, the device contact portion and the body contact portion may be formed by molding a hydrogel in both surfaces of the sheet member. Unlike the conventional electrode transmitting an electrical signal by point contact between a protrusion and a receiving portion, the electrode according to an aspect of the present invention may transmit an electrical signal by surface contact between the device contact portion and the terminal. Also, hydrogel itself has adhesive properties. Accordingly, the terminal or the biosignal measurement device may be attached onto the electrode without using a protrusion or snap.

A conventional electrode generally has to include a protrusion and a receiving portion. Accordingly, there is a limit in miniaturizing the electrode. However, according to various aspects of the present invention, it is possible to make a device contact portion and a body contact portion in various sizes and in various shapes. Also, the device and body contact portions may be formed in the shape of a flat board. Accordingly, a thickness thereof may be significantly reduced. Also, a signal transmission process from the skin to a circuit may be simplified. Accordingly, motion artifacts may be reduced.

According to another aspect of the present invention, there is provided a biosignal measurement device which can provide a plurality of electrode members on a single insulation sheet. Namely, at least one type of data may be measured via the single electrode by forming a plurality of holes in the sheet member and connecting a device contact portion and a body contact portion via each hole. In this instance, the device contact portion and the body contact portion, which are one-to-one connected to each other via the each hole, need to be electrically separated from other device contact portions and other body contact portions, but may be electrically connected to another device contact portion or body contact portion which is connected via another hole.

According to another aspect of the present invention, there is provided a biosignal measurement device using the above-described electrode. The biosignal measurement device may include a signal processing member and an electrode member.

The signal processing member includes a plurality of externally exposed terminals, an analog signal processing unit, an analog-to-digital (A/D) signal converter for converting an analog signal into a digital signal and a digital signal processing unit for processing the converted digital signal. The electrode member includes an insulation sheet having a plurality of holes, a plurality of device contact portions formed in the shape of a flat board on the top surface of the insulation sheet and insulated from each other, and a plurality of body contact portions formed in the shape of a flat board on the bottom surface of the insulation sheet insulated from each other and individually connected to each device contact portion via the hole. In this instance, the device contact portion and the body contact portion may be formed of a material which is both conductive and adhesive and is electrically connected to a terminal. Also, the device contact portion and the body contact portion may maintain an attachment state without using a protrusion.

According to another aspect of the present invention, a biosignal measurement device may electrically connect a bottom surface and a top surface of an electrode without forming a hole. For this, the electrode includes two types of insulation sheets so that the two types of insulation sheets may cover and expose a top surface and a bottom surface of an electrode member.

As an example, the electrode may include a first insulation sheet, at least one electrode member that is provided on the first insulation sheet, and a second insulation sheet that is provided on the electrode member. The electrode member is formed in the shape of a flat board on a top surface of the first insulation sheet, of which one end is formed on the first insulation sheet and another end is externally exposed away from the first insulation sheet. Since the electrode member is formed of a material which is both conductive and adhesive, the electrode member may temporarily maintain its attachment state to a device or a body. The second insulation sheet provided on the electrode member may be formed exposing the top surface of the one end of the electrode member and electrically isolating the top surface of the other end of the electrode member. When at least two electrode members are provided on the single insulation sheet, the electrode members may be arranged in an identical direction or in a different direction. According to the arrangement of the electrode member, the second insulation sheet may cover a portion of the top surface of the electrode member in an integrated form or in a separated form.

According to another aspect of the present invention, a biosignal measurement device may use a snap connected terminal in a gender shape together with a flat board connected terminal utilizing surface contact. Namely, when connecting a signal processing member and an electrode member, the two members may be electrically and mechanically connected to each other using the snap connected terminal. Also, the flat board connected terminal may be connected by a flat board connecting structure using surface contact. Accordingly, it may be possible to prevent the electrode member from bending due to an alignment error between the terminals. Also, since an initial attachment location between the signal processing member and the electrode member may be easily found using the snap connected terminal which is comparatively excellent in a mechanical connection, the signal processing member and the electrode member may be more securely combined with each other.

As an example, the signal processing member may include an externally exposed snap terminal and a flat board terminal adjacent to the snap terminal. Also, the electrode member may include an insulation sheet, a snap contact portion electrically and mechanically connected to the snap terminal on a top surface of the insulation sheet, a flat board contact portion electrically connected to the flat board terminal and formed of a material which is both conductive and adhesive, a first body contact portion electrically connected to the snap contact portion on a bottom surface of the insulation sheet, and a second body contact portion electrically connected to the flat board contact portion on the bottom surface of the insulation sheet. The snap contact portion and the first body contact portion of the electrode member may form a snap electrode member. Also, the flat board contact portion and the second body contact portion may form a flat board electrode member which is insulated from the snap contact member.

As described above, the snap contact portion and the first body contact portion of the snap electrode member may be electrically connected to each other at a hole formed on the insulation sheet. Also, the snap contact portion and the first body contact portion may be electrically connected to each other by surrounding the insulation sheet. Also, the flat board contact portion and the second body contact portion of the flat board electrode member may be connected to each other by the above-described method or other methods.

The snap contact portion may rotate when the snap contact portion is electrically connected to the snap terminal. A user may adjust a position using an inserted snap contact portion as an axis, so that other flat board contact portions or snap contact portions may be adjacent to a corresponding flat board terminal or snap terminal.

Also, the snap contact portion and the snap terminal may have a noncircular section, e.g. an oval and a polygon, to prevent rotation. When the user inserts a standard snap contact portion into a snap terminal corresponding to the standard snap contact portion, the user may complete the adjustment of the position.

Any one of the snap contact portion and the snap terminal may be a protrusion. In this case, the snap contact portion and the snap terminal may be mechanically combined with each other by elasticity or a self-force.

Additional and/or other aspects and advantages of the present invention will be set forth in part in the description which follows and, in part, will be obvious from the description, or may be learned by practice of the invention.

BRIEF DESCRIPTION OF THE DRAWINGS

The above and/or other aspects and advantages of the present invention will become apparent and more readily appreciated from the following detailed description, taken in conjunction with the accompanying drawings of which:

FIG. 13 is a top view illustrating an electrode and a biosignal measurement device according to still another embodiment of the present invention.

DETAILED DESCRIPTION OF THE EMBODIMENTS

Figure 1:
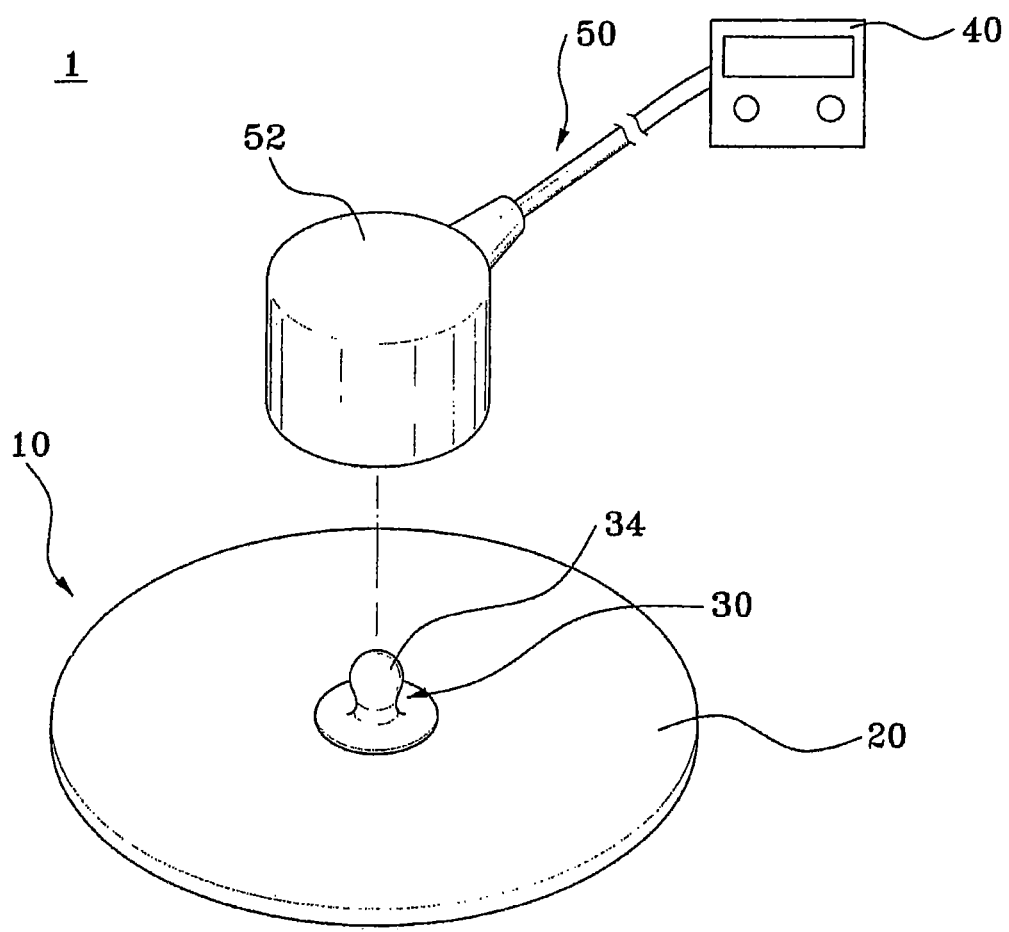
FIG. 1 is a perspective view illustrating a conventional electrode and biosignal measurement device.
Figure 2:
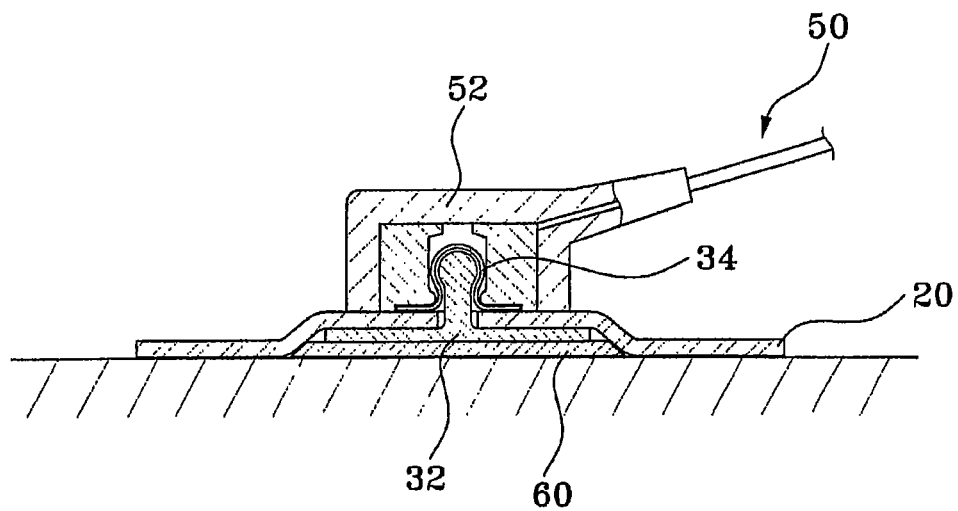
FIG. 2 is a cross-sectional view illustrating an attachment state of the electrode in FIG. 1.

Reference will now be made in detail to embodiments of the present invention, examples of which are illustrated in the accompanying drawings, wherein like reference numerals refer to the like elements throughout. The embodiments are described below in order to explain the present invention by referring to the figures.

Figure 3:
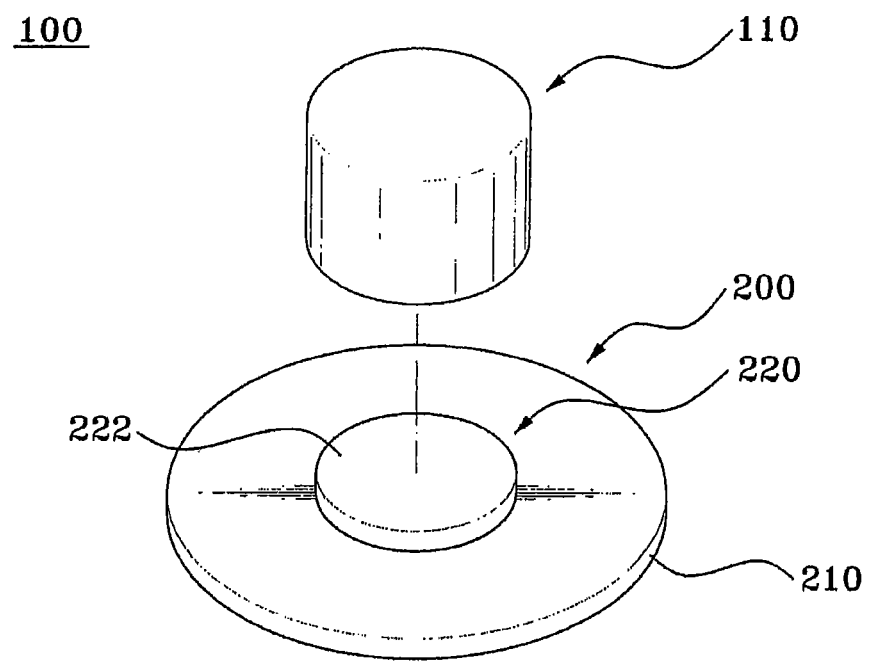
FIG. 3 is a perspective view illustrating an electrode and a biosignal measurement device according to an embodiment of the present invention.
Figure 4:
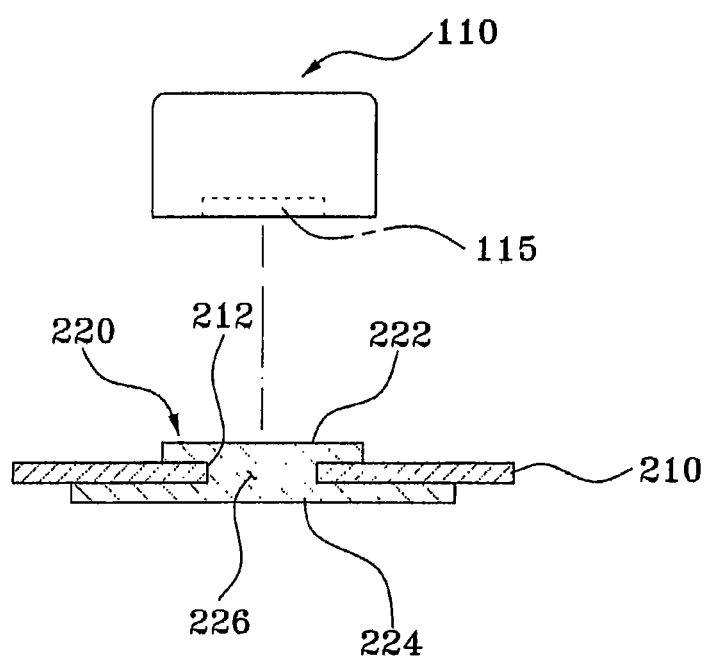
FIG. 4 is a cross-sectional view illustrating the electrode and the biosignal measurement device of FIG. 3.

FIG. 3 is a perspective view illustrating an electrode and a biosignal measurement device according to an embodiment of the present invention, and FIG. 4 is a cross-sectional view illustrating the electrode and the biosignal measurement device of FIG. 3.

Referring to FIGS. 3 and 4, a biosignal measurement device 100 includes a signal processing unit 110 and an electrode 200. The electrode 200 is attached onto a living body for measurement of biosignals and the signal processing unit 110 is placed on the electrode 200. An electrolysis cream including an electrolyte may be used for attaching the electrode 200 onto the living body. After spreading the electrolysis cream over the skin, the electrode 200 may be attached thereto. Also, the signal processing unit 110 is placed on the electrode 200. In this instance, a terminal 115 of the signal processing unit 110 is electrically connected to the electrode 200. The terminal 115 and the electrode 200 make surface contact by using their flat contact surfaces. Accordingly, the terminal 115 and the electrode 200 have the wide contact area. Also, since a wide surface is used, resistance may be reduced. Accordingly, a minute current in a living body may be effectively transmitted to the terminal 115 of the signal processing unit 110.

The electrode 200 includes an insulation sheet 210 and an electrode member 220.

The insulation sheet 210 is formed of a nonconductive or insulating material. Also, the insulation sheet 210 may be provided by using paper or insulating resin. The insulation sheet 210 is formed in the shape of a circle or a polygon. A hole 212 is formed in the center of the insulation sheet 210. The hole 212 may integrally connect portions of the electrode member 220. In this instance, each portion is provided on the top and bottom surfaces of the insulation sheet 210. The electrode member 220 includes a device contact portion 222 and a body contact portion 224, which are connected to each other via the hole 212.

In the present embodiment, one hole 212 is formed in one insulation sheet 210 and one electrode member 220 is provided. However, to collect various types of information at the same time, one electrode may measure changes with respect to various points. In this case, a plurality of holes is formed in one insulation sheet. The electrode member 220 corresponding to each hole may be individually provided. Also, a signal processing unit may include a plurality of terminals. In this case, each terminal may maintain a one-to-one relationship with each corresponding device contact portion and may be electrically connected thereto.

Referring again to FIGS. 3 and 4, the device contact portion 222 and the body contact portion 224 of the electrode member 220 are formed of a material which is both conductive and adhesive. The electrode member 220 may transmit a minute current from a living body to the signal processing unit 110. Also, since the device contact portion 222 has adhesive properties, the device contact portion 222 may be attached to the bottom surface of the signal processing unit 110. Although a combinational relationship between a protrusion and a groove as in the conventional art is not formed, adhesiveness may be effectively maintained. A material having conductive and adhesive properties may be variously selected, but a hydrogel is usually utilized.

The device contact portion 222 and the body contact portion 224 are integrally formed as a single body. This may be manufactured by molding a melted or fluidic hydrogel in both surfaces of the insulation sheet 210. More specifically, the device contact portion 222 and the body contact portion 224 may be provided by placing a fluidic hydrogel around the hole 212 and molding the fluidic hydrogel into a solid material which is both conductive and adhesive.

The insulation sheet 210 and the electrode member 220 may be flexibly transformable and easily attached onto an attachment area while taking on a shape of an attachment area. Also, to easily attach the electrode 200 onto a living body, an adhesive material may be placed around the insulation sheet 210 adjacent to the body contact portion 224.

The terminal 115 in the form of a metal may be exposed on the bottom surface of the signal processing unit 110. The signal processing unit 110 may be provided on the electrode 200 by placing the bottom surface of the signal processing unit 100 on the top surface of the device contact portion 222. In this case, the terminal 115 and the device contact portion 222 are closely attached to each other by surface contact. Accordingly, the terminal 115 and the device contact portion 222 may be electrically connected to each other via the wide surface. Through this, transmissibility between the device contact portion 222 and the terminal 115 may be improved. Also, a signal-to-noise (S/N) ratio may be improved.

Also, since the device contact portion 222 has adhesive properties, the device contact portion 222 may maintain a combined state with the signal processing unit 110 without using a combinational structure. The signal processing unit 110 may be connected to an external device in a wired or wireless manner. Also, while being attached onto a living body, the signal processing unit 110 may transmit biosignal data, such as an ECG, an EMG, an EEG, a GSR, etc., of a subject. In the conventional art, a combinational structure using a protrusion and a groove was used for attaching a signal processing unit to an electrode. However, in the present embodiment, the device contact portion 222 maintains a combined state by using adhesive properties of a hydrogel.

Referring to FIG. 4, the device contact portion 222 and the body contact portion 224 are connected via the hole 212. Structurally, the device contact portion 222 and the body contact portion 224 are electrically connected to each other via a hole connector 226 corresponding to the hole 212.

Figure 5:
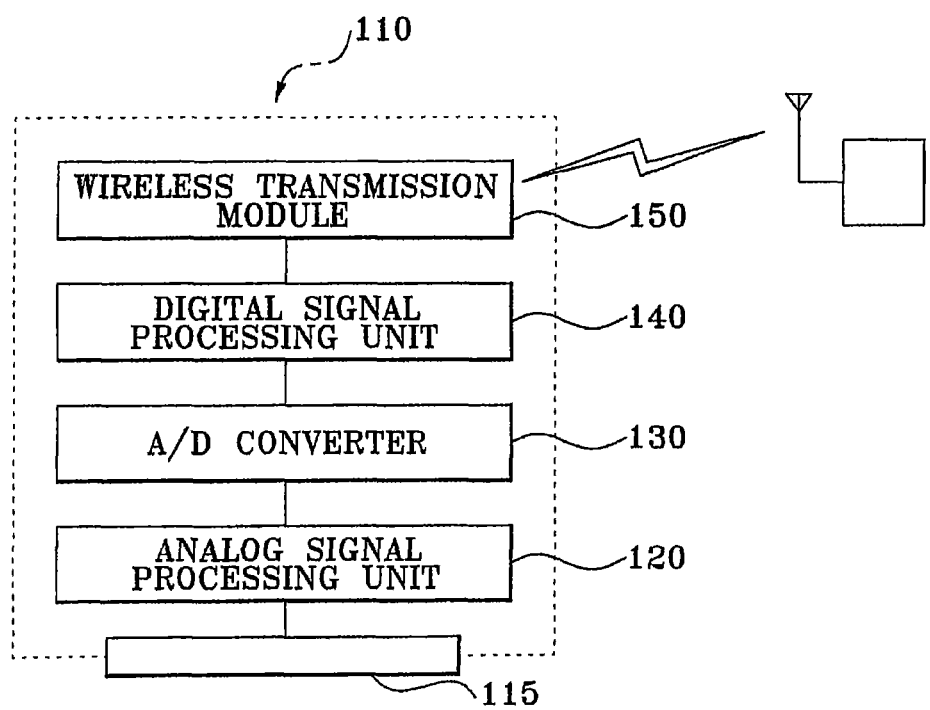
FIG. 5 is a diagram illustrating a function of a signal processing unit of FIG. 3.

FIG. 5 is a diagram illustrating a function of a signal processing unit of FIG. 3.

Referring to FIG. 5, the signal processing unit 110 includes an analog signal processing unit 120, an A/D converter 130, a digital signal processing unit 140 and a wireless transmission module 150, which are sequentially provided from the terminal 115. The analog signal processing unit 120 may amplify or filter a minute current of a living body transmitted from the terminal 115, that is, an analog signal and transmit the same to the A/D converter 130. The A/D converter 130 converts the transmitted analog signal into a digital signal. The digital signal processing unit 140 processes the converted digital signal according to a programmed method. Process results may be transmitted to an external device via the wireless transmission module 150 or may be stored in an internal memory (not illustrated).

Figure 6:
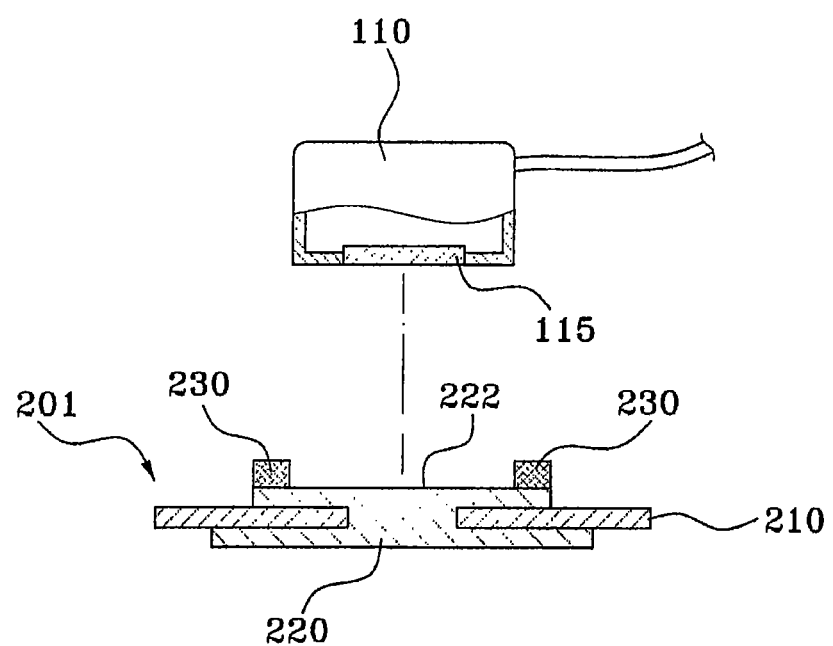
FIG. 6 is a partial cross-sectional view illustrating a biosignal measurement device and an electrode according to another embodiment of the present invention.

FIG. 6 is a partial cross-sectional view illustrating a biosignal measurement device and an electrode according to another embodiment of the present invention.

In this instance, a signal processing unit 110 and an electrode 201 of FIG. 6 are similar to the signal processing unit 110 and the electrode 200 of FIG. 5. The only difference is that the electrode 201 of FIG. 6 further includes device holders 230.

Referring to FIG. 6, the device holders 230 are provided on or around the device contact portion 222 to receive the edge of a lower portion of the signal processing unit 110. Accordingly, after placing the signal processing unit 110 on the device contact portion 222, the movement of the signal processing unit 110 may be limited by the device holders 230. Namely, the device holders 230 prevent the placed signal processing unit 110 from being easily separated from the electrode 201. Also, the device holder 230 is formed of a nonconductive material. Accordingly, the device holder 230 has insulating properties. Also, the device holder 230 may be formed of soft rubber or foam. Accordingly, the device holder 230 may produce friction for holding the signal processing unit 110.

In the present embodiment, the signal processing unit 110 is connected to an external device via a cable. Results processed by a digital signal processing unit may be transmitted to an external device via the cable.

Figure 7:
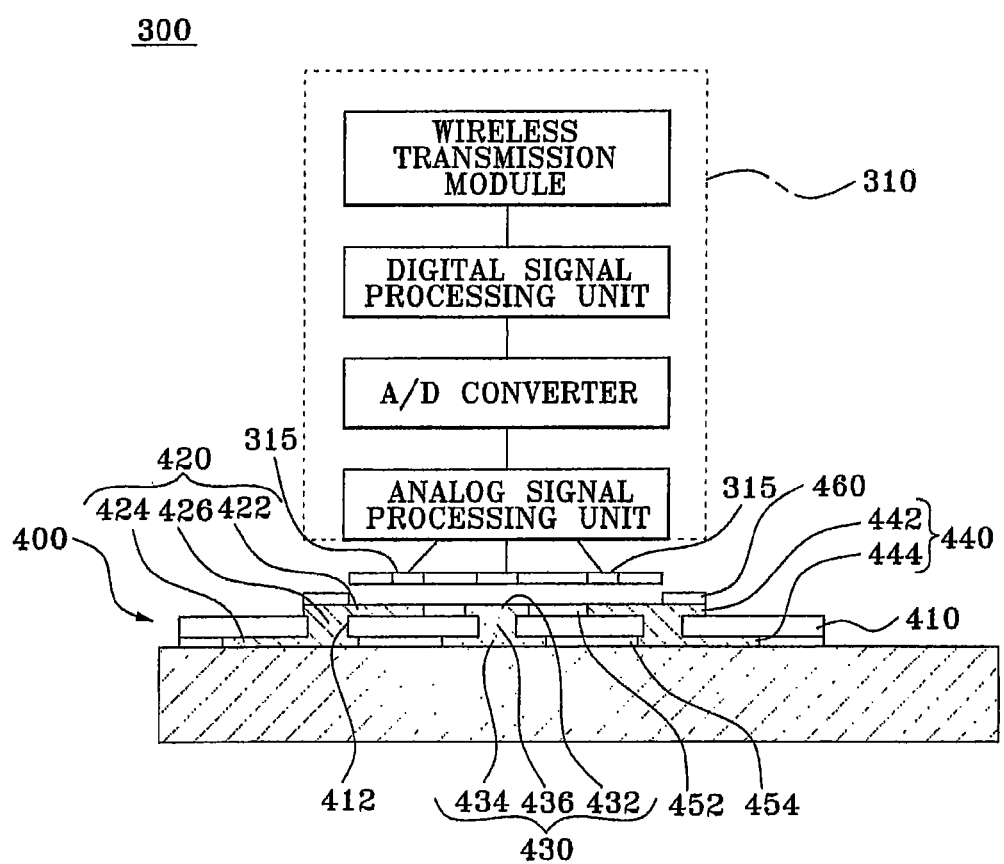
FIG. 7 is a cross-sectional view illustrating a biosignal measurement device and an electrode according to still another embodiment of the present invention.
Figure 8:
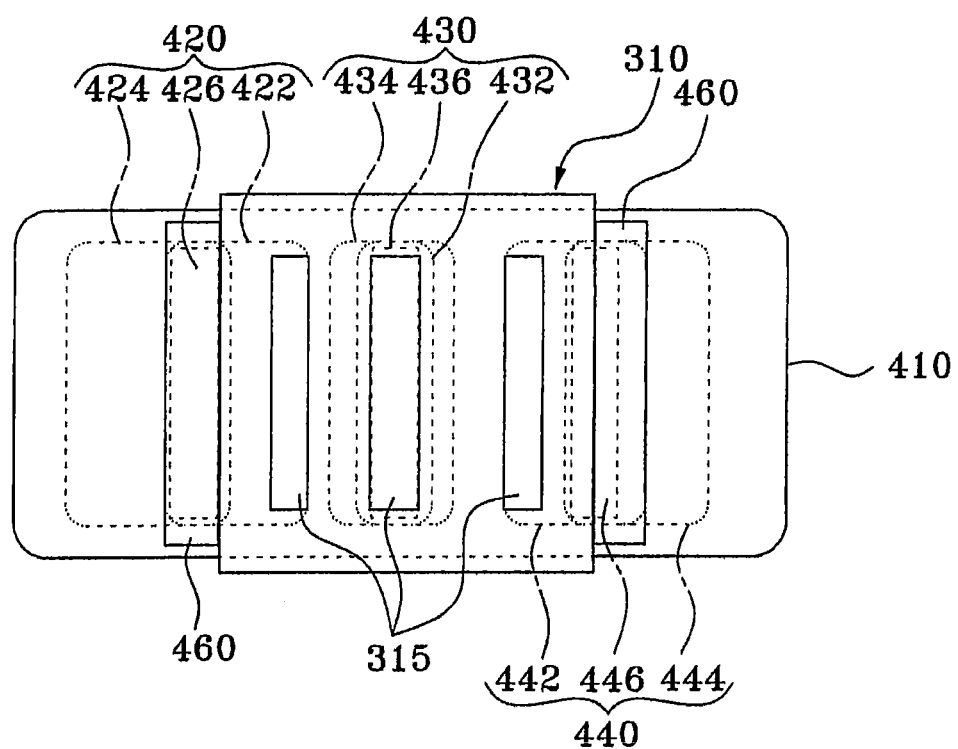
FIG. 8 is a top view illustrating the electrode and the biosignal measurement device of FIG. 7.

FIG. 7 is a cross-sectional view illustrating a biosignal measurement device and an electrode according to still another embodiment of the present invention, and FIG. 8 is a top view illustrating the electrode and the biosignal measurement device of FIG. 7.

Referring to FIGS. 7 and 8, a biosignal measurement device 300 includes a signal processing unit 310 and an electrode 400. The electrode 400 is attached onto a living body for measurement of biosignals and the signal processing unit 310 is placed on the electrode 400. An electrolysis cream including an electrolyte may be used for attaching the electrode 400 onto the living body. In this instance, three terminals 315 of the signal processing unit 310 are placed on the electrode 400. Each terminal 315 of the signal processing unit 310 is electrically connected to the electrode 400. Each terminal 315 and the electrode 400 make surface contact by using their flat contact surfaces. Accordingly, the terminal 315 and the electrode 400 have a wide contact area. Also, since a wide surface is used, resistance may be reduced. Accordingly, a minute current in a living body may be effectively transmitted to the terminal 315 of the signal processing unit 310.

The electrode 400 includes an insulation sheet 410 and electrode members 420, 430 and 440. The insulation sheet 410 is formed of a nonconductive or insulating material. Also, the insulation sheet 410 may be provided by using paper or insulating resin. The insulation sheet 410 is extended in the shape of a band. Three electrode members 420, 430 and 440 are provided side by side in the insulation sheet 410. In this instance, three holes 412, each shaped as a rectangle, are formed in the lengthwise direction of the insulation sheet 410. The holes 412 are to integrally connect portions of the electrode member 420. In this instance, each portion is provided on the top and bottom surfaces of the insulation sheet 410. Each of the electrode members 420, 430 and 440 includes each corresponding portion of device contact portions 422, 432 and 442 and body contact portions 424, 434 and 444, which are electrically connected to each other via each of the holes 412.

When the electrode member 420 is provided in the left side of the insulation sheet 410, the device contact portion 422 and the body contact portion 424 are connected via the hole connector 426. In this case, the hole connecter 426 is formed in the hole 412. The device contact portion 422 and the body contact portion 424 constructing the electrode member 420 are electrically connected to each other via the hole connector 426 by using a material which is both conductive and adhesive, such as a hydrogel. The electrode member 420 senses a biosignal from an area corresponding to the left side of the insulation sheet 410. The electrode member 440 provided in the right side of the insulation sheet 410 has a symmetrical structure to the electrode member 420 provided in the left side thereof.

The electrode member 430 is provided in the center of the insulation sheet 410. Also, the electrode member 430 includes the device contact portion 432 and the body contact portion 434, which are electrically connected to each other via the hole connector 436.

Referring to FIG. 7, the device contact portion 422 and the body contact portion 424 of the electrode member 420 are provided diagonal to each other. In this instance the device contact portion 422 and the body contact portion 424 are electrically connected to each other via the hole 412.

A device contact portion and a body contact portion may be provided to have the same center or diagonal to each other in upper and lower portions of an electrode member. For example, the device contact portion 432 and the body contact portion 434 of the central electrode member 430 are vertically positioned to have the same center, however the device contact portion 422 and the body contact portion 424 of the central electrode member 420 are divergently positioned to have the different center.

Also, a device contact portion and a body contact portion may have a different area in upper and lower portions of an electrode member. Accordingly, irrespective of a position and an interval of the body contact portions 424, 434 and 444, a position of the device contact portions 422, 432 and 442 may be changed. Also, the device contact portions 422, 432 and 442 may be centralized in a desired area. When centralizing the device contact portions 422, 432 and 442, the signal processing unit 310 may be made in a small size. Accordingly, the biosignal measurement device may be further miniaturized.

The electrode members 420, 430 and 440 may sense a biosignal from each corresponding area and transmit the biosignal to the signal processing unit 310. Also, because of the adhesive properties, the device contact portions 422, 432 and 442 may be attached onto the bottom surface of the signal processing unit 310 and maintain effective adhesiveness. A material having conductive and adhesive properties may be variously selected, but a hydrogel is usually utilized.

As illustrated in FIG. 7, the insulation members 452 may be provided around the device contact portion 422, 432 and 442. In this case, each of the insulation members 452 has the same or less thickness as one of the adjacent device contact portion 422, 432, and 442. Also, the insulation members 452 may support the bottom surface of the signal processing unit 310 together with the device contact portions 422, 432 and 442. The insulation member 452 may be formed of a material which is nonconductive and adhesive. Accordingly, the insulation members 452 may insulate the device contact portions 422, 432 and 442, because of nonconductive properties. Also, the insulation members 452 may be attached onto the signal processing unit 310 with the device contact portions 422, 432 and 442, because of adhesive properties.

A contact portion or an adhesive agent having insulating properties may be provided on the bottom surface of the insulation sheet 410 and around the body contact portions 424, 434 and 444. In the present embodiment, an insulation attaching member 454 is provided. The insulation attaching member 454 may attach the electrode 400 to the skin with the body contact portions 424, 434 and 444.

The terminals 315 in the form of a metal are provided side by side on the bottom surface of the signal processing unit 310. The bottom surface of the signal processing unit 310 is placed on the device contact portions 422, 432 and 442. In this manner, the signal processing unit 310 may be placed on the electrode 400 and each terminal 315 and each of the corresponding device contact portions 422, 432 and 442 make surface contact with each other. Namely, each terminal 315 and each of the corresponding device contact portions 422, 432 and 442 are electrically connected to each other by a large surface area. Accordingly, the terminal 315 and the corresponding device contact portion 422, 432 and 442 may be electrically connected to each other. Also, the device contact portions 422, 432 and 442 are insulated from each other, so an individual connection between the terminal 315 and one of the corresponding device contact portion 422, 432 and 442 may be maintained. Through this, transmissibility between the corresponding device contact portion 422, 432 and 442 and the terminal 315 may be improved. Also, a signal-to-noise (S/N) ratio may be improved.

Also, the device contact portions 422, 432 and 442 have adhesive properties. Accordingly, the device contact portions 442, 432 and 442 may maintain a combined state with the signal processing unit 310 while not having a combination structure. The signal processing unit 310 may be connected to an external device in a wired or wireless manner. Also, while being attached onto a living body, the signal processing unit 310 may transmit biosignal data of a subject, such as an ECG, an EMG, an EEG, a GSR, etc. In the conventional art, a combinational structure using a protrusion and a groove is used for attaching a signal processing unit onto an electrode. However, in the present embodiment, the device contact portions 422, 432 and 442 maintain a combined state by using adhesive properties of a hydrogel.

The signal processing unit 310 includes an analog signal processing unit, an A/D converter, a digital signal processing unit and a wireless transmission module, which are sequentially provided from the terminal 315. The analog signal processing unit receives a biosignal from three terminals and transmits the biosignal to the A/D converter after amplification or filtering. The A/D converter converts the transmitted analog signal into a digital signal. The digital signal processing unit processes the converted digital signal according to a programmed method. Process results may be transmitted to an external device via the wireless transmission module.

The device holders 460 are provided on or around the device contact portions 422 and 442 to receive the edge of a lower portion of the signal processing unit 310. Accordingly, after placing the signal processing unit 310 on the device contact portions 422, 432 and 442, the signal processing unit 310 may be more securely held by the device holders 460. Also, the device holder 460 is formed of a nonconductive material. Accordingly, the device holder 460 has insulating properties. Also, the device holder 460 may be formed of soft rubber or foam. Accordingly, the device holder 460 may produce friction for holding the signal processing unit 310.

In the present embodiment, the signal processing unit 310 is connected to an external device via a cable. Results processed by a digital signal processing unit may be transmitted to the external device via the cable.

Figure 9:
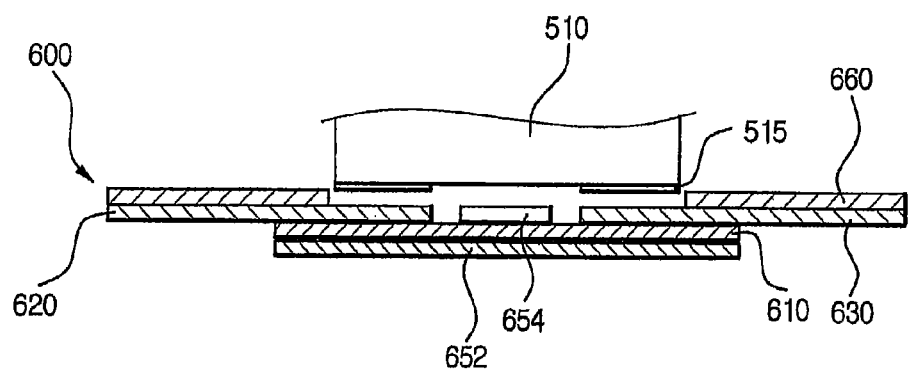
FIG. 9 is a cross-sectional view illustrating a biosignal measurement device and an electrode according to an embodiment of the present invention.
Figure 10:
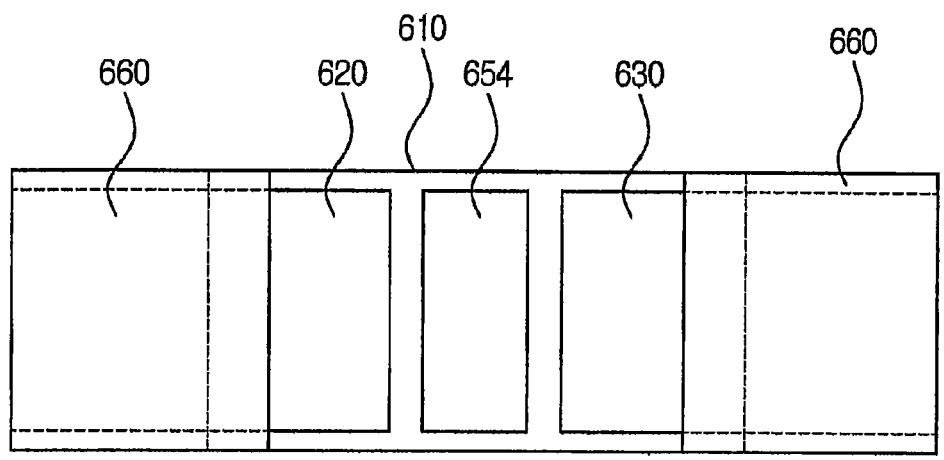
FIG. 10 is a top view illustrating the electrode of FIG. 9.

FIG. 9 is a cross-sectional view illustrating a biosignal measurement device and an electrode according to an embodiment of the present invention, and FIG. 10 is a top view illustrating the electrode of FIG. 9.

Referring to FIGS. 9 and 10, a biosignal measurement device 500 includes a signal processing unit 510 and an electrode 600. The electrode 600 is attached onto a living body for measurement of biosignals and the signal processing unit 510 is placed on the electrode 600. Also, two terminals 515 of the signal processing unit 510 are placed on the electrode 600. Each terminal 515 of the signal processing unit 510 is electrically connected to the electrode 600. Each terminal 515 and the electrode 600 make surface contact by using their flat contact surfaces. Also, since a wide surface is used, resistance may be reduced.

The electrode 600 includes an insulation sheet 610 and electrode members 620 and 630. The insulation sheet 610 is formed of a nonconductive or insulating material. Also, the insulation sheet 610 may be provided by using paper or insulating resin. Two electrode members 620 and 630 are provided on opposite sides of the insulation sheet 610 and partially laid on its top surface. The electrode members 620 and 630 are jutted out and externally exposed from both ends of the insulation sheet 610. Also, other insulation sheets 660 are provided on a top surface of the electrode members 620 and 630.

Unlike the above-described embodiments, the insulation sheet 610 has no hole. The electrode members 620 and 630 may have a body contact portion and a device contact portion, respectively. The body contact portion of them may be an outside portion externally exposed from a bottom surface of the insulation sheet 610 and facing downward, and the device contact portion of them may be an inside portion internally exposed portion from the insulation sheet 660 and facing upward.

Since both the electrode members 620 and 630 are formed of a material which is conductive and adhesive, such as a hydrogel, the electrode 600 may be attached onto a living body. Also, since the device contact portions of the electrode member 620 and 630 are centrally gathered, the size of the signal processing unit 510 may be reduced. Also, the size of the biosignal measurement device 500 may be further reduced.

The electrode members 620 and 630 may sense a biosignal from each corresponding area and transmit the biosignal to the signal processing unit 510. Also, because of the adhesive properties of the electrode members 620 and 630, the signal processing unit 510 may be attached to the device contact portions of them.

Also, an adhesive material 652 is provided on the bottom surface of the insulation sheet 610 to improve adhesive strength between the electrode 600 and a living body and another adhesive material 654 is provided between the electrode members 620 and 630 to improve adhesive strength between the electrode 600 and the signal processing unit 510.

The two metal terminals 515 are closely provided on the bottom surface of the signal processing unit 510 and insulated from each other. The bottom surface of the signal processing unit 510 is placed on the device contact portion of the electrode members 620 and 630. In this manner, the signal processing unit 510 may be placed on the electrode 600 and each terminal 515 and each corresponding device contact portion make surface contact with each other.

The signal processing unit 510 includes an analog signal processing unit, an A/D converter, a digital signal processing unit and a wireless transmission module, which are sequentially provided from the terminal 515. The analog signal processing unit receives a biosignal from three terminals and transmits the biosignal to the A/D converter after amplification or filtering. The A/D converter converts the transmitted analog signal into a digital signal. The digital signal processing unit processes the converted digital signal according to a programmed method. Process results may be transmitted to an external device via the wireless transmission module.

Figure 11:
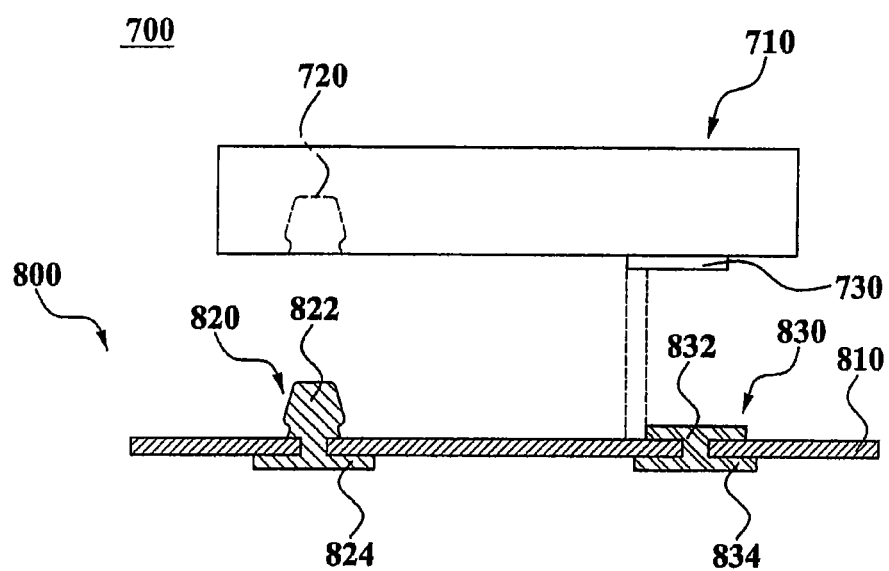
FIG. 11 is a cross-sectional view illustrating an electrode and a biosignal measurement device according to an embodiment of the present invention.

FIG. 11 is a cross-sectional view illustrating an electrode and a biosignal measurement device according to an embodiment of the present invention.

Referring to FIG. 11, a biosignal measurement device 700 includes a signal processing unit 710 and an electrode 800. The electrode 800 is attached onto a living body for measurement of biosignals and the signal processing unit 710 is placed on the electrode 800 and may process or transmit information from the electrode 800.

A snap terminal 720 and a flat board terminal 730 are provided on a bottom surface of the signal processing unit 710. The snap terminal 720 corresponds to a snap contact portion 822 of the electrode 800 to receive the snap contact portion 822 and be electrically and mechanically connected thereto. The flat board terminal 730 corresponds to a flat board contact portion 832 of the electrode 800 and may be electrically connected to the flat board contact portion 832. As shown in FIG. 11, the snap contact portion 822 is a protrusion and the snap terminal 720 is formed as a groove to receive and fix the snap contact portion 822. Also, a projection is formed in a lower portion of the snap terminal 720 and a groove is formed in a lower portion of the snap contact portion 822. Accordingly, the snap terminal 720 and the snap contact portion 822 may maintain a secure combination state.

In the present embodiment, the snap terminal 720 and the snap contact portion 822 are mechanically combined with each other by physical engagement using elasticity. However, the snap terminal 720 and the snap contact portion 822 may be mechanically combined with each other using magnetism and a magnetic substance.

The flat board terminal 730 is provided on a bottom surface of the signal processing unit 710. The flat board contact portion 832 corresponding to the flat board terminal 730 is provided on a top surface of the electrode 800. The flat board contact portion 832 is formed of a material which is both conductive and adhesive, e.g. a hydrogel, and may maintain its electrical connection state with the flat board terminal 730. The adhesive property of the flat board contact portion 832 may prevent the flat board terminal 730 from becoming separated. Also, the adjacent snap contact portion 822 maintains a more stable combination state with the snap terminal 720. Accordingly, the signal processing unit 710 and the electrode 800 may maintain a stable attachment state.

Also, a combination location between the signal processing unit 710 and the electrode 800 may be easily determined by the snap terminal 720 and the snap contact portion 822 which are the protrusion and the groove, respectively. Accordingly, a user may initially insert the snap terminal 720 into the snap contact portion 822 and stably attach the signal processing unit 710 and the electrode 800.

When connecting a plurality of terminals using a snap connecting structure, a combination between the terminals may be difficult or an electrode may be misaligned due to a manufacturing defect. However, a signal processing unit and an electrode may be stably attached by tolerating a certain amount of error when using the snap connecting structure together with a flat board connecting structure.

The electrode 800 includes an insulation sheet 810, the snap contact portion 822 and the flat board contact portion 832 on the top surface of the insulation sheet 810, and a first body contact portion 824 and a second body contact portion 834 on the bottom surface of the insulation sheet 810. The snap contact portion 822 and the first body contact portion 824 may be electrically connected to each other via a hole on the insulation sheet 810. Also, the flat board contact portion 832 and the second body contact portion 834 may be electrically connected to each other via another hole on the insulation sheet 810.

The snap contact portion 822 and the first body contact portion 824 may be formed of a metal and form a single snap electrode member 820. Also, the flat board contact portion 832 and the second body contact portion 834 may be formed of a hydrogel and form a single flat board electrode member 830. Also, the snap contact portion 822 and the first body contact portion 824 may be formed of different materials. Also, the flat board contact portion 832 and the second body contact portion 834 may be formed of different materials.

Although not illustrated, the signal processing unit 710 may include an analog signal processing unit, an A/D converter, a digital signal processing unit and a wireless transmission module, which are sequentially provided from the terminal 720. The analog signal processing unit may receive a biosignal from the terminals 720 and 730 and transmit the biosignal to the A/D converter after amplification or filtering. The A/D converter may convert the transmitted analog signal into a digital signal. The digital signal processing unit may process the converted digital signal according to a programmed method. Process results may be transmitted to an external device via the wired/wireless transmission module.

Figure 12:
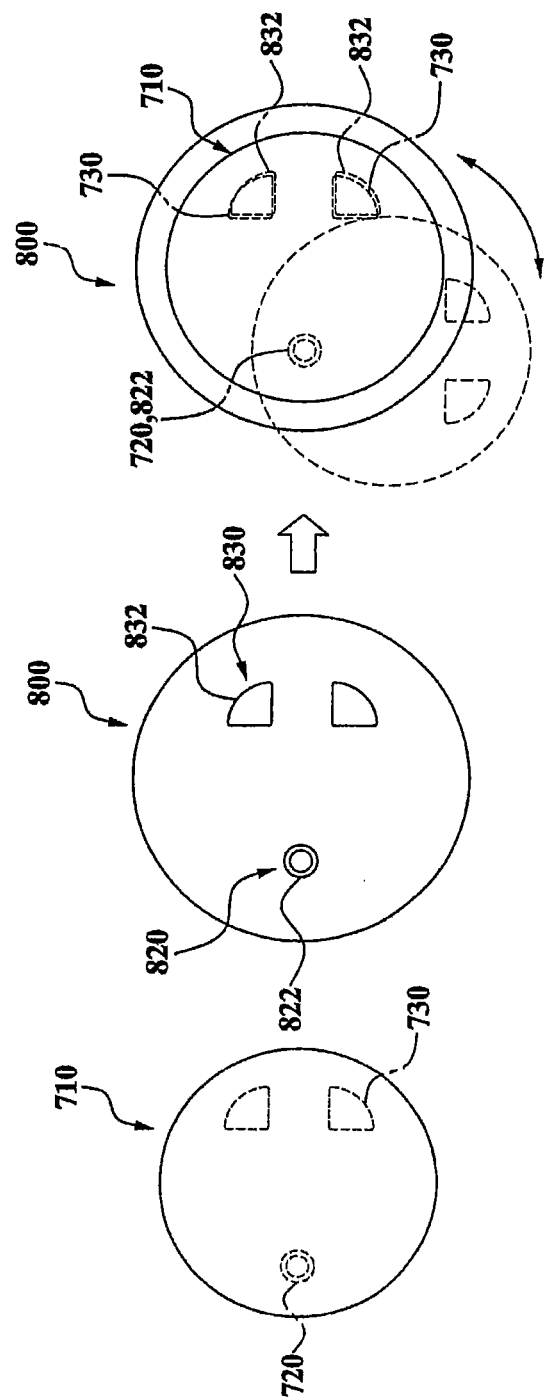
FIG. 12 is a top view illustrating an electrode and a biosignal measurement device according to another embodiment of the present invention.

FIG. 12 is a top view illustrating an electrode 800 and a biosignal measurement device according to another embodiment of the present invention, and FIG. 13 is a top view illustrating an electrode 800 and a biosignal measurement device according to still another embodiment of the present invention.

In FIGS. 12 and 13, a signal processing unit 710 and an electrode 800 are separated from each other on the left and the signal processing unit and the electrode are combined with each other on the right.

Referring to FIG. 12, a snap terminal 720 and a snap contact portion 822 may have a circular section. Since a portion of the snap contact portion 822, connected to the signal processing unit 710, has the circular section, the signal processing unit 710 may rotate on the snap contact portion 822. Accordingly, a user may initially combine the snap terminal 720 with the snap contact portion 822 and rotate the signal processing unit 710, so that the flat board terminal 730 and the flat board contact portion 832 may be connected to each other in an appropriate position.

However, referring to FIG. 13, a signal processing unit 710' and an electrode 800' may be properly attached in only a certain position. For this, a snap terminal 720' and a snap contact portion 822' may have a noncircular shape, e.g. an oval, a square and a pentagon. Since a portion of the snap contact portion 822' connected to the signal processing unit 710' has a noncircular section, the signal processing unit 710' may be inserted into the snap contact portion 822' in only the certain direction. In this case, the signal processing unit 710' may not rotate on the snap contact portion 822'. Accordingly, the user may attach the signal processing unit 710' and the electrode 800 in an appropriate position by combining the snap terminal 720' and the snap contact portion 822' in a proper position.

An electrode according to the above-described embodiments of the present invention may maintain a stable connection with a terminal or a signal processing unit. Also, the electrode may make surface contact with the terminal or the signal processing unit. Accordingly, a minute current may be smoothly transmitted from a living body to the electrode. Also, since a stable connection is maintained, noise is reduced and a signal-to-noise (S/N) ratio may be improved.

Also, according to the above-described embodiments of the present invention, a plurality of electrodes may be provided on one pad. A position, size and shape of a contact portion may be arbitrarily determined. Accordingly, a miniaturized and slimmed down product may be manufactured.

Also, a biosignal measurement device according to the above-described embodiments of the present invention may utilize advantages of both a snap connected terminal and a flat board connected terminal by using the snap connected terminal together with the flat board connected terminal using surface contact. Namely, when connecting a signal processing member and an electrode member, the two members may be electrically and mechanically connected to each other using the snap connected terminal. Also, the flat board connected terminal may be connected by a flat board connecting structure using surface contact. Accordingly, it may be possible to prevent the electrode member from bending due to an interval error between the terminals.

Also, according to the above-described embodiments of the present invention, an initial attachment location between the signal processing member and the electrode member may be easily found using the snap connected terminal which is comparatively superior in a mechanical connection, and the signal processing member and the electrode member may be more securely combined with each other.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. An electrode for transmission between a biosignal measurement device and a living body, comprising:
   an insulation sheet having a plurality of holes; and
   a plurality of electrode members each formed of a material which is both conductive and adhesive and being insulated from each other, each of the electrode members including a device contact portion in a shape of a flat board on a top surface of the insulation sheet, a body contact portion in a shape of a flat board on a bottom surface of the insulation sheet, and a hole connector connecting the device contact portion and the body contact portion of each electrode member at respective ones of the holes.

2. A biosignal measurement device for making contact with a living body and measuring a biosignal, comprising:
   a signal processing member comprising a plurality of externally exposed terminals, an analog signal processing unit processing an analog signal transmitted from the plurality of terminals, an analog-to-digital (A/D) signal converter converting the analog signal into a digital signal, and a digital signal processing unit processing the converted digital signal; and an electrode member comprising an insulation sheet having a plurality of holes, a plurality of device contact portions each formed in a shape of a flat board on a top surface of the insulation sheet and insulated from each other and a plurality of body contact portions in a shape of a flat board on a bottom surface of the insulation sheet, insulated from each other and individually connected to corresponding device contact portions at respective ones of the holes, the device contact portion and the body contact portion formed of a material which is both conductive and adhesive, wherein the electrode member and the terminals are electrically connected to each other by surface contact.

3. A biosignal measurement device for making contact with a living body and measuring a biosignal, comprising:

a signal processing member comprising an externally exposed snap terminal and a flat board terminal adjacent to the snap terminal; and an electrode member comprising an insulation sheet, a snap contact portion electrically and mechanically connected to the snap terminal on a top surface of the insulation sheet, a flat board contact portion electrically connected to the flat board terminal and formed of a material which is both conductive and adhesive, a first body contact portion electrically connected to the snap contact portion on a bottom surface of the insulation sheet, and a second body contact portion electrically connected to the flat board contact portion on the bottom surface of the insulation sheet.

4. The device of claim 3, wherein the signal processing member further comprises an analog signal processing unit processing an analog signal transmitted from the snap terminal and the flat board terminal, an A/D signal converter converting the analog signal into a digital signal, and a digital signal processing unit processing the converted digital signal.

5. The device of claim 3, wherein the snap contact portion is a protrusion, and the snap contact portion is inserted into the snap terminal to be mechanically fixed and electrically connected.

6. The device of claim 3, wherein the snap contact portion is rotatably connected to the snap terminal.

7. The device of claim 3, wherein the snap contact portion has a noncircular section and maintains a fixed state with respect to the snap terminal.

8. The device of claim 3, wherein the snap contact portion and the snap terminal have corresponding uneven shapes and are mechanically connected to each other using a magnet.

9. An electrode for transmission between a biosignal measurement device and a living body, comprising:

an insulation sheet;

a snap electrode member including a snap contact portion on a top surface of the insulation sheet and a first body contact portion electrically connected to the snap contact portion on a bottom surface of the insulation sheet; and a flat board electrode member including a flat board contact portion formed of a material which is both conductive and adhesive on the top surface of the insulation sheet and a second body contact portion electrically connected to the flat board contact portion on the bottom surface of the insulation sheet.

10. The electrode of claim 9, wherein the snap contact portion is a protrusion.

11. The electrode of claim 9, wherein a portion of the snap contact portion, which is adapted to be connected to the biosignal measurement device, has one of a circular section and a noncircular section.

12. The electrode of claim 9, wherein the snap contact portion includes a magnet or a magnetic substance which is adjacent to the snap contact portion which is adapted to be connected to the biosignal measurement device.

\* \* \* \* \*